United States Patent [19]

Zucker

[11] Patent Number: 5,086,782
[45] Date of Patent: Feb. 11, 1992

[54] SYRINGE FOR WITHDRAWAL OF FLUIDS

[76] Inventor: Jerry Zucker, 16 Buckingham Dr., Charleston, S.C. 29407

[21] Appl. No.: 622,552

[22] Filed: Dec. 5, 1990

[51] Int. Cl.⁵ .............................................. A61B 5/00
[52] U.S. Cl. .................................................... 128/765
[58] Field of Search .............. 128/760, 763, 765, 766; 604/231

[56] References Cited

U.S. PATENT DOCUMENTS

| | | | |
|---|---|---|---|
| 3,978,846 | 9/1976 | Bailey | 128/765 |
| 4,004,575 | 1/1977 | Sarstedt | 128/765 |
| 4,660,570 | 4/1987 | Dombrowski | 128/765 |
| 4,813,433 | 3/1989 | Downey | 128/765 |

*Primary Examiner*—Max Hindenburg
*Attorney, Agent, or Firm*—Juettner Pyle & Lloyd

[57] ABSTRACT

A syringe for withdrawal of fluids by compression of the plunger toward the needle by a single hand includes a fluid inlet leading from the needle to the upper part of a cylinder and piston, and a plunger extending out of the lower end of the cylinder and upwardly.

4 Claims, 1 Drawing Sheet

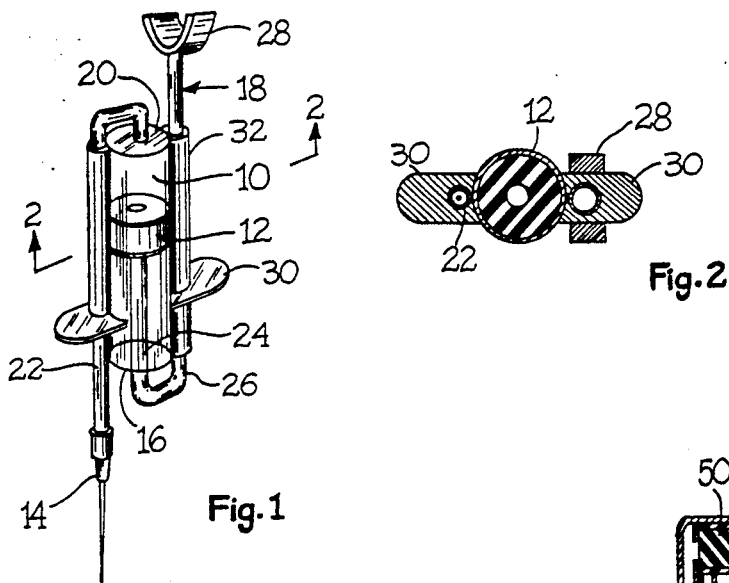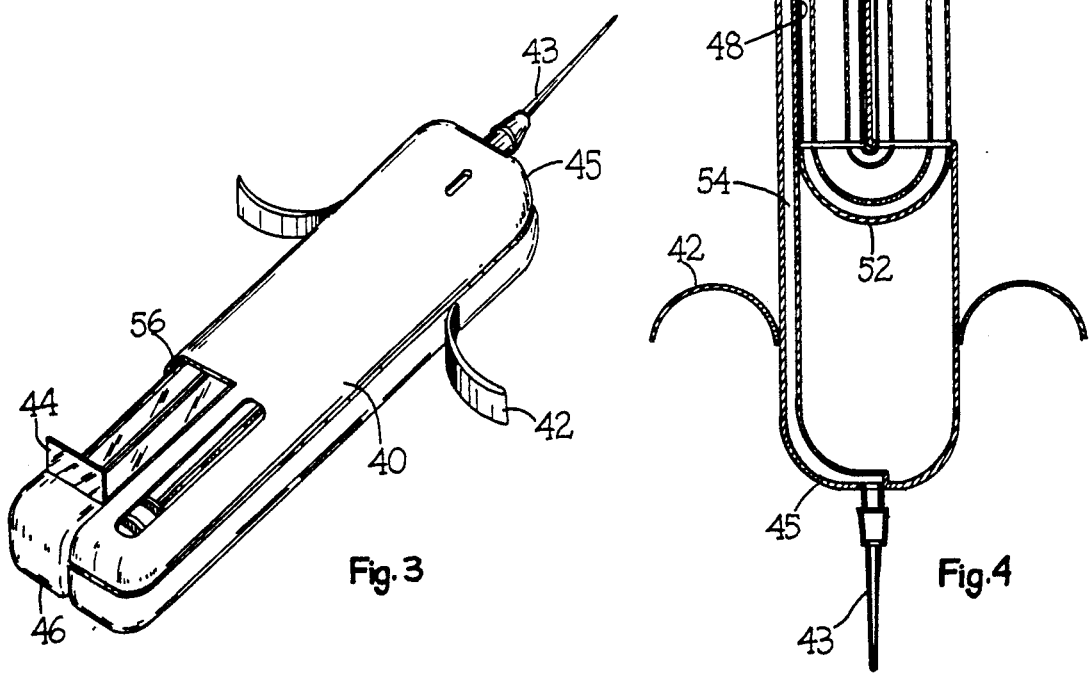

SYRINGE FOR WITHDRAWAL OF FLUIDS

BACKGROUND OF THE INVENTION

This invention relates to syringes and more particularly to such devices which are capable of being operated by one hand and which are used to withdraw liquid, such as blood samples, from animals.

Conventional syringes comprise a cylinder having an apertured needle at one end and a piston in the cylinder, with the piston being connected to a rod extending from the other end. In order to withdraw liquids, it is necessary to hold the cylinder in one hand and pull the rod with the other. It would be desirable to provide a syringe which is capable of withdrawing fluids upon compression of the piston, which would allow for one handed operation with the use of finger tabs on the cylinder.

The U.S. Pat. No. 4,813,433 discloses a syringe having a pair of connected chambers, with a piston and rod in one of the chambers. Forward movement of the piston in one chamber causes reduced pressure in the other chamber, the latter being connected to a hollow needle. This concept requires a particular seal for the shaft, which may not be particularly reliable, or may expose the liquid compartment to non-sterile conditions. German patent No. 621145 discloses the use of a reverse action gear on the syringe plunger whereby a pushing action on the plunger is translated into a pulling action on the piston.

SUMMARY OF THE INVENTION

In accordance with the present invention, a cylinder is equipped with a piston having a rod extending toward the needle end of the cylinder and having a U-shaped portion and leg extending back outside the cylinder and terminating in a plunger end. The needle is connected to a passage leading to the other end of the cylinder. Compression of the plunder end toward the cylinder causes reduced pressure in the passage connected to the needle and enables withdrawal of liquids with a one hand grasping operation.

THE DRAWINGS

FIG. 1 is a perspective view of a first embodiment of the present invention.

FIG. 2 is a sectional view through line 2—2 of FIG. 1.

FIG. 3 is a perspective view of a second embodiment of the present invention.

FIG. 4 is a longitudinal sectional view of the embodiment shown in FIG. 3.

DESCRIPTION OF THE PREFERRED EMBODIMENTS

FIG. 1 illustrates a syringe assembly comprising a cylinder or tube 10 having a cylindrical bore and having a circular piston 12 in slidable sealing engagement with the bore. The assembly includes a syringe needle 14 extending away from one open end 16 of the cylinder, and a thumb plunder 18 extending away from the other closed end 20 of the cylinder. The needle is connected to a tube 22 or passage extending externally along the length of the cylinder and is connected to the plunger end 20 of the cylinder and in fluid tight connection therewith. Movement of the piston 12 toward the end 16 and the needle 14 causes reduced pressure in the tube 22 and allows withdrawal of liquids through the tube and into the upper portion of the cylinder.

The plunger, generally indicated at 18, is U-shaped, with one portion or leg 24 connected to the piston 12 through the open end 16 of the cylinder 10, and the other portion or leg 26 extending along the exterior of the cylinder in a generally coaxial relation and having an enlarged terminus or thumb grip 28 at the end. Finger tabs 30 are secured to the cylinder and extend laterally outward or generally perpendicular to the axis of the cylinder. A tubular guideway 32 may be secured to the side of the cylinder 10, coaxial therewith, to slidably receive and guide the outer leg 26 of the plunger.

It may be seen that since the plunger 18 is connected to the exhausted side of the piston 12 and the needle 14 is connected to the vacuum side, movement of the plunger downwardly into the top end of the cylinder without any possibility of contamination from outside sources, or by the piston rod or plunger entering a sterile zone of the cylinder.

It will be apparent that the U-shaped plunger can take other forms, including more than one leg extending upwardly, or an external tube connected to the leg 24.

FIGS. 3 and 4 illustrate another version enclosed in an elongated housing 40 having medial finger tabs 42 and a syringe or hollow needle 43 extending from one end 45 and a thumb tab 44 near the other end 46. The housing surrounds a tube 48 having a cylindrical bore with a piston 50 therein. The piston 50 is connected to a U-shaped plunger rod 52 having the legs thereof extending in parallel. A passage 54 extends within the housing to the vacuum end of the cylinder, i.e., on the side of the piston 50 opposite to that which is connected to the plunger 52. A slot or opening 56 is provided in the housing 40 to enable movement of the plunger toward the needle. As shown, the entire side of the unit or one side may be pushed to move the plunger toward the needle.

I claim:

1. A syringe for the withdrawal of fluids, said syringe comprising a cylinder, said cylinder having first and second ends, a hollow needle extending away from said first end of said cylinder, a piston slidable in said cylinder from said second end toward said first end thereof and toward said needle, a passage connecting said needle to the second end of the cylinder in fluid tight relation, and a plunger, said plunger comprising a first portion connected to said piston and extending in said cylinder toward said first end, and a second portion connected with said first portion and extending exteriorly of said cylinder toward said second end.

2. The syringe of claim 1 comprising an enlarged terminus on the second portion of said plunger to enable pushing with the thumb.

3. The syringe of claim 2 further comprising finger tabs extending laterally from said cylinder, said finger tabs being spaced from said terminus.

4. The syringe of claim 1 wherein said plunger is U-shaped.

* * * * *